(12) United States Patent
Fallek

(10) Patent No.: US 8,469,918 B2
(45) Date of Patent: Jun. 25, 2013

(54) METHOD AND APPARATUS FOR PERFORMING INJECTIONS WHILE VIBRATING THE SKIN

(76) Inventor: Steve Fallek, Englewood, NJ (US)

(\*) Notice: Subject to any disclaimer, the term of this patent is extended or adjusted under 35 U.S.C. 154(b) by 79 days.

(21) Appl. No.: 13/052,283

(22) Filed: Mar. 21, 2011

(65) Prior Publication Data
US 2011/0288471 A1  Nov. 24, 2011

Related U.S. Application Data

(60) Provisional application No. 61/347,512, filed on May 24, 2010.

(51) Int. Cl.
*A61B 17/20* (2006.01)

(52) U.S. Cl.
USPC .............................. 604/22; 600/583; 433/118

(58) Field of Classification Search
USPC ............................... 604/22; 600/583; 433/118
See application file for complete search history.

(56) References Cited

U.S. PATENT DOCUMENTS

| | | | |
|---|---|---|---|
| 5,647,851 A | | 7/1997 | Pokras |
| 6,099,503 A | * | 8/2000 | Stradella ..................... 604/135 |
| 6,602,229 B2 | | 8/2003 | Coss |
| 7,244,266 B2 | | 7/2007 | Garthe et al. |
| 2004/0204662 A1 | * | 10/2004 | Perez et al. .................. 600/583 |
| 2009/0004628 A1 | * | 1/2009 | Knutson ..................... 433/215 |

\* cited by examiner

*Primary Examiner* — Kevin C Sirmons
*Assistant Examiner* — Emily Schmidt
(74) *Attorney, Agent, or Firm* — Gottlieb, Rackman & Reisman, P.C.

(57) ABSTRACT

An apparatus is provided for performing an injection, the apparatus including a front end, a vibrator mechanism selectively vibrating the front end during an injection and a syringe holder holding a syringe during an injection through the front end while the front end is vibrated.

7 Claims, 4 Drawing Sheets

METHOD AND APPARATUS FOR PERFORMING INJECTIONS WHILE VIBRATING THE SKIN

RELATED APPLICATIONS

This application claims priority to application Ser. No. 61/347,512 filed May 24, 2010 and incorporated herein by reference in its entirety.

BACKGROUND OF THE INVENTION a. Field of Invention

This application pertains to a method and apparatus for performing injections, and more particularly to an apparatus that applies a vibration as a skin stimulation selected to reduce pain during the injection.

b. Description of the Prior Art

Injections are one of the most common ways used by doctors and other health care providers to introduce drugs into a patient. Traditionally, injections are typically performed using a syringe with a needle attached to a barrel filled with the appropriate drug. The needle is first inserted through the skin (either on the arm, or other parts of the body), and then a piston is advanced manually forcing the drug to be expressed through the needle into the patient's tissues. Alternatively, the drug is fed to the needle through a long tube attached either to an IV tube directly or through a pumping mechanism.

Regardless of which system is used, one problem with all injections have been that they require the piercing of the skin and the subcutaneous tissues lying immediately under the skin. Since the skin and the subcutaneous tissues are laced with numerous nerves, during the piercing step, the patient feels discomfort and pain. Depending on the individual, the injection site, the size of the needle and other factors, the discomfort and pain could be mild or could be very severe. Children and infants are particularly susceptible and, hence, they very often fear injections and administrating an injection in such cases could be a tough experience for both the doctor and the parent.

Attempts have been made to resolve these problems but they have not been successful. For example, it has been suggested that the syringe be vibrated during injection. Of course, this solution is unacceptable because a vibrating syringe can be difficult to hold. Moreover, a vibrating needle tears the tissues during injection, causing much more harm than good. Other attempts made use of devices with vibrating needles. These attempts are also unacceptable from a mechanical view since it is difficult and expensive to make such a device and from a medical view as discussed above.

SUMMARY OF THE INVENTION

The present inventor has found that the discomfort and pain suffered at the beginning of an injection can be eliminated or significantly reduced if just prior to and/or during an injection, vibration or other similar mechanical excitation is applied to the skin and the subcutaneous tissues at the injection site. It is believed that this action can either confuse or mask—the nerve endings and their pathways so that the nerves will not transmit impulses to the brain resulting in discomfort or pain.

Briefly, a device constructed in accordance with this invention includes:

a housing having an aperture sized and shaped to accept a syringe with a needle and a front section with a tip, said tip having an opening through which the needle is selectively extended from the housing for administering of an injection; and a vibrating mechanism disposed within said housing and adapted to selectively vibrate said front section during said injection.

Preferably the housing includes a first chamber for accepting a portion of the syringe during the injection, said chamber being in communication with said aperture and said opening and holding said syringe during said injection. The housing may also include a second chamber, said vibrating mechanism being disposed in said second chamber. In one advantageous embodiment, the vibrating mechanism includes a motor having a rotating shaft with a weight having an off-axis center of gravity, and a switch selectively activating said motor.

The housing includes a third chamber holding a battery for providing current to the motor.

A syringe holder may be provided that extends into the aperture and configured to hold the syringe, the syringe holder being selectively movable between a first position in which the syringe needle is disposed inside the housing and a second position in which needle extends outwardly of said housing.

When the vibrating mechanism is activated, it causes at least a front part of the housing to vibrate. A care provider loads a syringe having a barrel with a drug into the housing, activates the vibrating mechanism and positions the housing so that it is contact with a patient's skin at a desired injection site. At least the front portion of the housing vibrates thereby making the nerve endings in the skin at the injection somewhat insensitive to pain. The needle is then advanced so that it extends from the housing penetrating the skin until it reaches the desired injection zone. The drug is then expelled from the syringe in a normal manner.

DETAILED DESCRIPTION OF THE INVENTION

Figure 1:
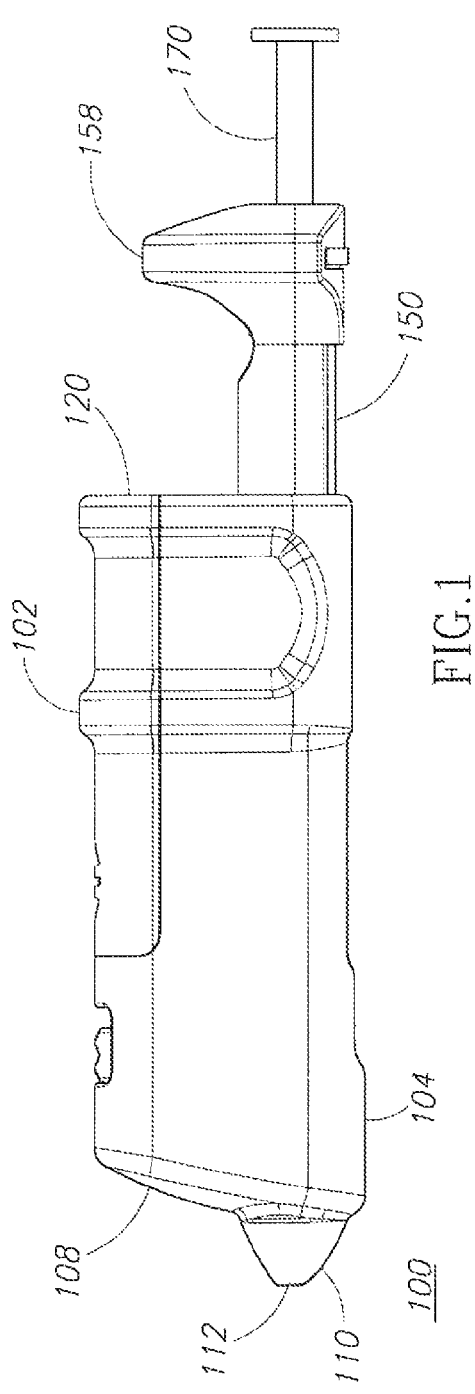
FIG. 1 shows a side view of an injection apparatus constructed in accordance with this invention.

As shown in the drawings, an apparatus 100 constructed in accordance with this invention includes a housing 102 with a sidewall wall 104. The housing 102 can be made in a single piece by molding or can be made from two segments 102A, 102B joined together by a screw 106. The housing can be made of a transparent material or a bottom portion 108 of the housing is transparent window 106.

Housing 102 is formed with a front section defined by a front section outer wall 108 that is generally closed and includes a conical extension end or tip 110 having an opening 112. The opening 112 is preferably circular and has a diameter D.

Housing 102 further includes a rear wall 120 that is generally flat with a large opening or aperture 122. Aperture 122 is aligned with opening 112. The sidewall 104 extends longitudinally between the front section outer wall 108 and the rear wall.

The interior of the housing 102 defined by sidewall 104 is partitioned into three chambers: a battery chamber 124, a motor chamber 126 and a syringe chamber 128. A top portion 130 of the housing is removable to give access to chamber 124. Chamber 124 is used to house a removable standard battery (typically an AAA battery) 132. Also contained within the chamber 124 are a spring terminal 136 and a flat terminal 138 that contact the positive and negative terminals of the battery 132 in the normal manner. The battery chamber is disposed behind the motor chamber and the the battery and motor chambers 124, 126 are radially offset from the syringe chamber, as shown.

Chamber 126 houses an electric motor 140 having a shaft 142 with a weight 144. Chamber 126 further includes a switch 148 operated by a switch cover 146 slidably mounted on wall 106. Moving the switch cover 146 in one direction closes the switch 148 which in turn provides power to the motor 140 from battery 132. Moving the switch cover 146 in the opposite direction turns the motor off. The weight 144 is not rotationally symmetrical but instead it is configured so that its center of gravity is offset from the axis of the shaft of the motor 140. As a result, when the motor 140 is turned on, it causes the weight to rotate and this action causes the front section of the housing 102, including conical extension 110 to vibrate laterally. Preferably, the apparatus is configured so that the motor 140 rotates at about 15000 RPM and causes the conical section to vibrate gently at a small amplitude of less than $\frac{1}{16}"$.

Figure 4:
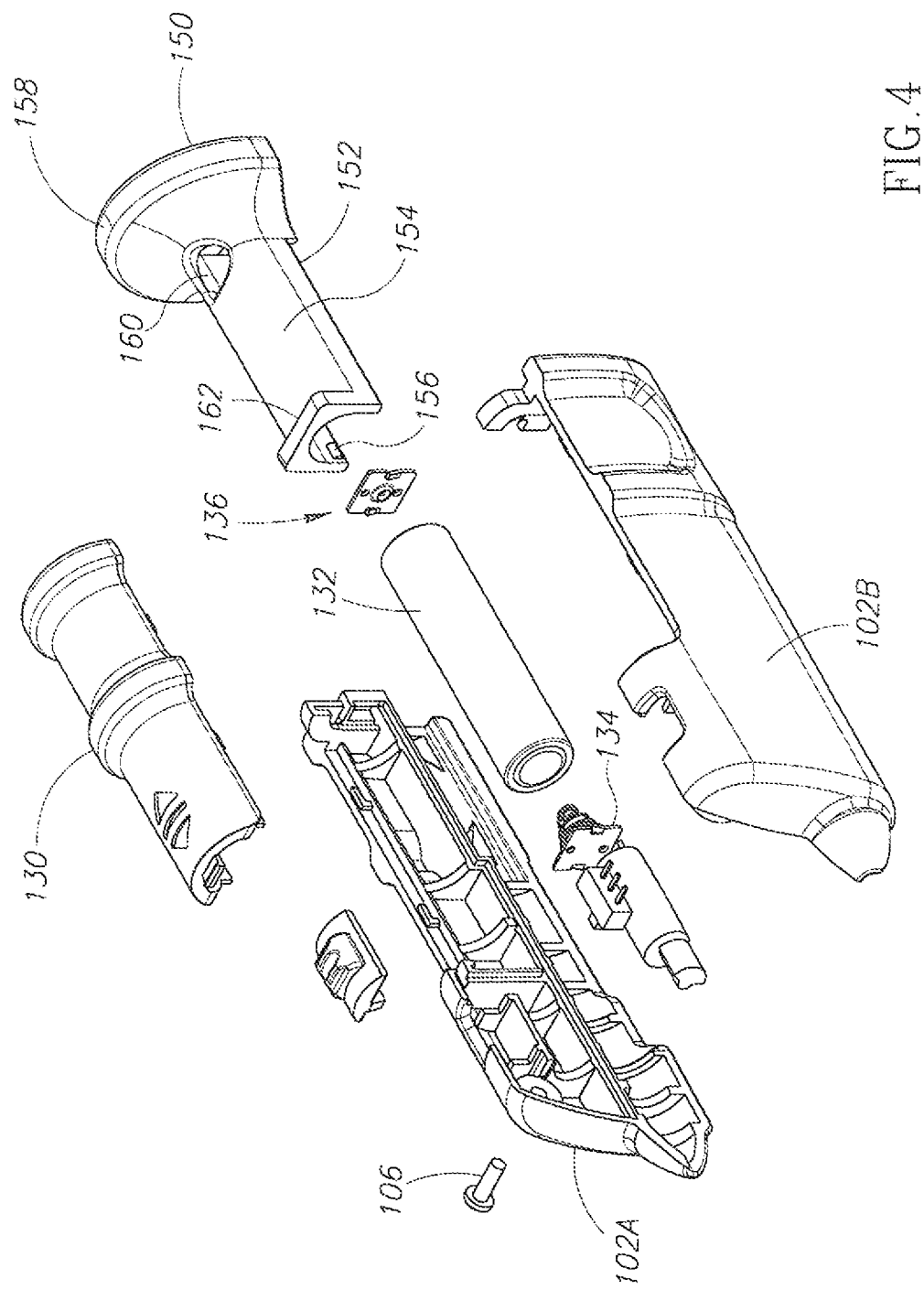
FIG. 4 shows an exploded view of the apparatus of FIGS. 1-3.
Figure 5:
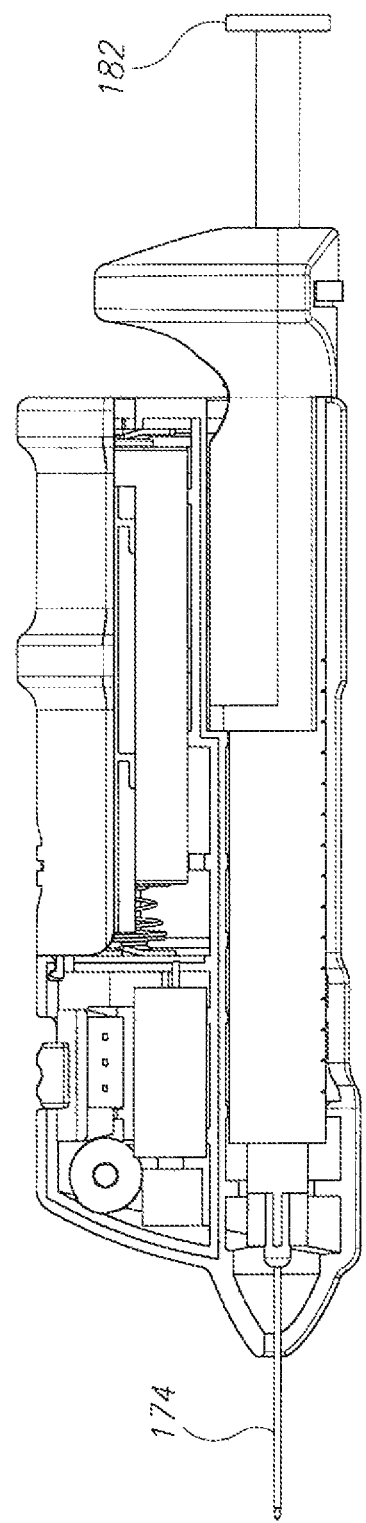
FIG. 5 shows a side view with the needle fully extended through the housing.

Chamber 128 houses a portion of a syringe holder 150. As best seen in FIG. 4, this syringe holder 150 has an elongated portion 152 having an outer surface 154. A semi-cylindrical longitudinal channel 156 extends through the holder 150. The syringe holder 150 further includes an enlarged head 158 attached to one end of portion 152. A window 160 is formed in the portion 152 adjacent to the head 158. Opposite head 158, the portion 152 is formed with a tab 162. The portion 152 is sized and shaped to fit through opening 122. The tab 162 is provided to trap the portion 152 to insure that the syringe holder 150 does not fall out and get lost. The syringe holder 150 is configured so that its portion 152 can be moved back and forth axially through the chamber 128.

Figure 2:
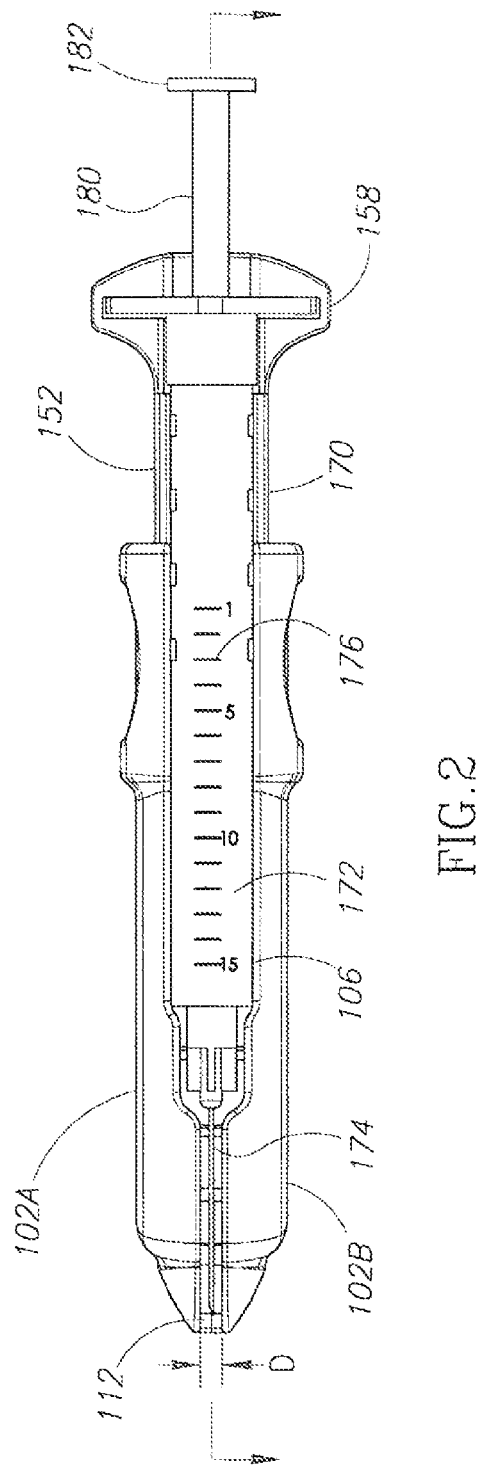
FIG. 2 shows a bottom view of the apparatus of FIG. 1.
Figure 3:
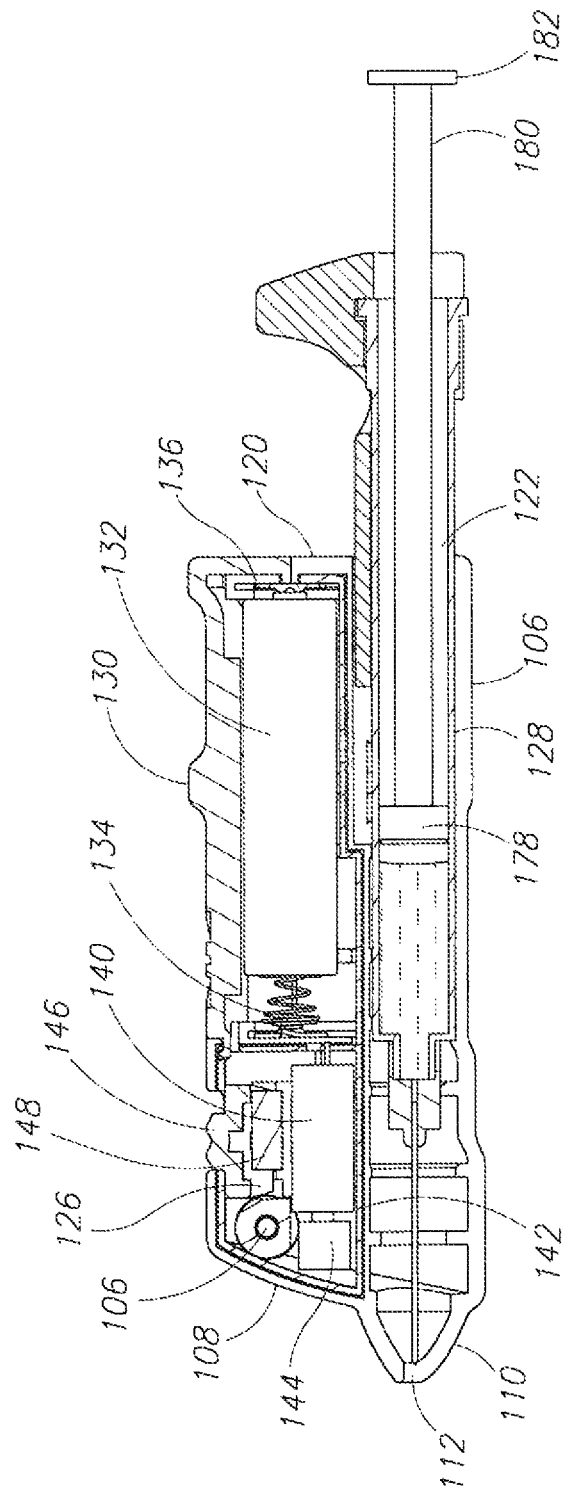
FIG. 3 shows a side sectional view with the injection apparatus being introduced into the housing.

Preferably, the channel 156 is sized and shaped to form an interference fit with the barrel of a typical syringe, such as a conventional 1cc syringe 170 available from Becton Dickinson. As shown in FIG. 2, such a conventional syringe 170 includes a barrel 172 terminating with a replaceable needle 174. The barrel 172 has gradations 176 to indicate the progress of an injection and the amount of fluid that has been expelled from the barrel 172. Disposed inside the barrel is a piston 178 (see FIG. 3) that is attached to a shaft 180. The shaft 180 is terminated with a thumb pad 182. The syringe holder is axially and selectively slidable within said syringe chamber between a first position and second position. In said first position the needle tip is disposed adjacent to said opening 112 inside the syringe chamber. In the second position of the syringe holder, the needle passes through the opening and at least partially exposed. The syringe chamber 128 has a longitudinal axis passing through said aperture 122 and said opening 112, and the motor includes a motor shaft extending in parallel with said axis and an off center weight 144 mounted on said motor shaft, the rotation of said off center weight 144 causing a selective lateral vibration of said front section 108 when said motor 140 is activated.

The apparatus 100 is operated as follows. First the syringe 170 is loaded with an appropriate drug (or any other substance that a health care provider desires to inject into a patient). The loaded syringe is then inserted into syringe holder 150 so that its barrel 172 is held tightly and securely by the channel 156. In this configuration, the needle 174 is completely contained within the apparatus 100, and the health care provider, as well as the patient and others around the patient are protected from injury. In addition, the needle is hidden from view of a potentially anxious patient at all times. The barrel 172 and its gradations 176 are visible through the transparent wall 106.

Next, the motor 140 is turned on by switch 148 causing the front end and conical section 110 to vibrate transversally with respect to the longitudinal axis of the syringe 170. The tip of the conical section 110 is placed in contact with the skin of the patient at the site of injection. The vibration of the conical section is transferred to the skin of the patient and the tissues underlying the skin.

The health care provider holds the apparatus 100 in this position with two fingers and then pushes the enlarged head 158 with his thumb axially toward the front of the apparatus 100 thereby causing the syringe to move forward with the needle 174 extending outwardly of the conical section 110. Since the conical section is touching the skin at the site of the injection, as the needle is advanced, it penetrates the vibrated skin and the tissues to the predetermined depth. Next, the health care provider shifts his thumb from the enlarged head 158 to the thumb pad 182 and starts pushing it inward to inject the contents of the barrel. During this time, the conical section 110 keeps on vibrating thereby confusing the nerve pathways of the skin and tissues and reducing or eliminating pain to the patient. Preferably the diameter D of opening 112 is sized so that is large enough to insure that as the conical section 110 vibrates, it does not touch needle 174 and therefore the vibration is not transmitted to the needle itself. The motor can be kept on until the injection is completed and the needle is withdrawn, or can be turned off any time before or after, thereafter stopping the vibration.

It should be appreciated that the whole process can be performed with one hand holding the apparatus 100 while the skin can be held and manipulated with the other hand as needed. If multiple sites are injected sequentially, the needle can be retracted first, the conical section 112 can be moved to a new site, and the needle can then be extended again. Once the process is completed, the syringe is removed from the holder 150 and at least its tip can be disposed. The conical section 102 is wiped with alcohol or other disinfectant and the apparatus 100 is ready to be used again.

The apparatus can be sized and shaped to so that it can be used with several syringes of similar sizes, e.g. 1, 3 or 5 cc, needles from 18 to 25 gauges and injection depth of up to ½ in or more. An apparatus with somewhat larger housing is needed for syringes of 3, 5, 10, 20 or 60 ccs.

As illustrated in the Figures, the apparatus can be made with only five parts having special shapes and sizes, the rest of the parts being of standard shapes and sizes.

The apparatus can be used for many different procedures including pediatric treatments, anesthesia, cosmetic treatments, drawing blood and blood donations, treatments for diabetes, veterinarian treatments, vaccines, etc.

Obviously numerous modifications may be made to the claims without departing from its scope as defined in the appended claims. For example the housing can be easily adapted to work with automated injection devices.

I claim:

1. An injection apparatus for performing an injection using a standard syringe having a standard syringe body, a needle with a needle tip and a plunger terminating in a thumb pad opposite the needle, said injection apparatus comprising:

a housing having an end with an aperture, a front section formed by a front section outer wall disposed opposite said aperture and having a tip, said tip having an opening sized and shaped to selectively receive the needle;

a sidewall extending longitudinally between said front section and said end to define a syringe chamber that is closed except for said aperture and said opening, and a motor chamber, said motor chamber being radially offset from said syringe chamber;

a syringe holder having a channel shaped and sized to engage the body of the standard syringe with thumb pad extending outwardly of the syringe holder, said syringe holder being sized and shaped to fit removably through said aperture with said syringe body and needle being disposed in said syringe body, said syringe holder being axially and selectively slidable within said syringe chamber between a first and a second position, wherein said needle tip is disposed adjacent to said opening inside said syringe chamber and wherein said needle passes through said opening and is at least partially exposed for an injection toward said second position; and a vibrating mechanism including a motor disposed within said motor chamber, said vibrating mechanism being adapted to selectively vibrate said front section during said injection.

2. The apparatus of claim 1 wherein said vibrating mechanism includes an electric motor rotating an off-set weight and a switch selectively activating said motor.

3. The apparatus of claim 1 wherein said side wall further defines a battery chamber holding a battery for selectively activating said motor, said battery chamber being axially oriented behind said motor chamber and in parallel to said syringe chamber.

4. The apparatus of claim 1 wherein said outer front wall and said tip have together a conical shape.

5. The apparatus of claim 1 wherein said syringe chamber has a longitudinal axis passing through said aperture and said opening, and said motor includes a motor shaft extending in parallel with said axis and an off center weight mounted on said motor shaft, the rotation of said off center weight causing a selective lateral vibration of said front section when said motor is activated.

6. A method of performing an injection of a substance into a patient using a vibrating apparatus having a housing with a syringe chamber, a motor chamber and a tip disposed in front of said syringe chamber, said tip being laterally offset from said motor chamber, said tip having an opening, said apparatus further including a syringe holder movable into and out of said syringe chamber along a longitudinal axis passing through said opening, said method comprising the steps of:

inserting a barrel of a standard syringe with a needle, a plunger and a thumb pad into said syringe holder, said barrel being filled with a substance;

inserting said holder with said barrel into said syringe chamber, with said needle disposed inside the syringe holder so that said needle is being pointed toward said opening;

positioning the housing with said front tip in contact with the patient's skin at the site of injection;

causing said tip of the vibrating apparatus in contact with the patient's skin to vibrate to cause the skin and patient tissues to vibrate laterally with respect to the longitudinal axis d the needle;

advancing said needle through said opening;

inserting said needle into the patient tissues at the injection site; and expelling the substance through the needle.

7. The method of claim 6 wherein the needle is advanced to the site by advancing said syringe holder in said housing.

* * * * *